US006716397B2

(12) United States Patent
Astle (10) Patent No.: US 6,716,397 B2
(45) Date of Patent: Apr. 6, 2004

(54) ELUTER FOR SOLID PHASE EXTRACTION SYSTEM

(76) Inventor: Thomas W. Astle, 607 Harbor View Rd., Orange, CT (US) 06477

( * ) Notice: Subject to any disclaimer, the term of this patent is extended or adjusted under 35 U.S.C. 154(b) by 181 days.

(21) Appl. No.: 09/752,272

(22) Filed: Jan. 2, 2001

(65) Prior Publication Data

US 2002/0084214 A1 Jul. 4, 2002

(51) Int. Cl.[7] ............................................. B01D 35/12
(52) U.S. Cl. ..................... 422/101; 210/445; 210/447; 422/119
(58) Field of Search ........................... 210/198.3, 227, 210/264, 445, 447; 422/63, 101, 119

(56) References Cited

U.S. PATENT DOCUMENTS

| | | | | |
|---|---|---|---|---|
| 5,260,028 A | * | 11/1993 | Astle | 422/101 |
| 5,510,025 A | * | 4/1996 | Benesi | 210/227 |
| 5,648,266 A | * | 7/1997 | Astle | 422/101 |
| 6,149,871 A | * | 11/2000 | Guirguis et al. | 422/101 |

* cited by examiner

Primary Examiner—Ivars C. Cintins
(74) Attorney, Agent, or Firm—John H. Crozier (57) ABSTRACT

In a preferred embodiment, an eluter instrument for an SPE system, including: a housing; an upper seal mounted in the housing for up and down motion with respect thereto; a lower seal mounted in the housing for up and down motion with respect thereto, and the upper seal and the lower seal being moveable between a first position in which the upper seal and the lower seal are spaced apart and not in proximity and a second position in which the upper seal and the lower seal are in proximity and spaced apart sufficiently only to clamp therebetween a first area of a plurality of areas of an SPE medium, the first area containing therein one or more compounds of interest, such as to permit elution of the one or more compounds of interest to another instrument.

10 Claims, 11 Drawing Sheets

ELUTER FOR SOLID PHASE EXTRACTION SYSTEM

BACKGROUND OF THE INVENTION

1. Field of the Invention.

The present invention relates to solid phase extraction generally and, more particularly, but not by way of limitation, to a novel eluter for a solid phase extraction system method that simultaneously aspirates multiple samples to be processed by solid phase extraction through a unique defined area for each sample in the defined area to contain various solid phase extraction elements, without an intervening liquid transfer step, and eluting the samples to an analyzer.

2. Background Art.

High performance liquid chromatography (HPLC) and mass spectrography (MS) are commonly used for the analysis of various chemical products. HPLC and MS have the unique ability to identify specific chemical entities within a mixture of components. A very common use is in drug research and development in the pharmaceutical industry.

In many cases, it is mandatory that the sample be pre-processed or "cleaned up" using solid phase extraction (SPE), prior to HPLC or MS. This is normally done by passing the sample through a silica bed. There are different silicas depending on the desired end product. C18 is a common SPE grade of silica and there are others. The component of interest, normally a chemical compound (e.g., a drug) is present mixed with other components within the sample. To analyze the compound of interest, it must first have some form of separation from the rest of the sample. Otherwise, the signal-to-noise ratio would be such that the component of interest could not be detected with sufficient precision.

SPE is the typical technique that is employed. The unique aspect of this technique is that the retention of the compound is a function of the solvent flowing through the silica. Thus, an aqueous solution flowing through the silica will cause certain compounds to be retained. If an organic solvent is then passed through the silica, the retained compound can be released or eluted into the solvent. This is SPE—the use of silica to separate compounds of interest from other materials.

In the late 1980's, cartridges of silica came on to the market. A common format used was the barrel of a 10 mL disposable syringe. In the middle to late 1990's, the need for higher throughput moved solid phase extraction to the 96-well format of microplates. The 10 mL syringe barrels were replaced by the columns in a deepwell microplate. This facilitated processing the samples through the silica columns with a 96-well pipettor.

Recently, 3M Company introduced its Empore® product in the 96-well format. This consists of silica supported in a Teflon® matrix. One advantage of this construction is that it provides for very small volume retention This is of critical importance as the total volume of the sample becomes smaller. Empore® elements are located in the bottoms of the SPE columns. Other techniques use more silica within the column. The end result serves the same purpose.

The incoming samples normally arrive in a 96-well format, although other formats can be employed as well Using individual or multi-well pipettors, the 96 samples are transferred to the 96 SPE columns Vacuum is used to move the samples through the silica. The compounds of interest are then retained on the silica, with the balance of the streams going to waste.

The next step is to place a capture plate under the SPE columns. Then, solvent of choice is added to the columns using the pipettor Vacuum is again used to create flow through the SPE columns This time, however, the eluent is captured in individual wells under each respective SPE column These 96 extracted samples are then transported to a sampling device that injects each sample individually into an analyzer. This normally is an HPLC instrument or an MS instrument or a combination of HPLC and MS instruments.

It will be appreciated that the above conventional techniques require a three-step process that involves three different types of equipment as well as involving multiple handling of the sample materials Accordingly, it is a principal object of the present invention to provide an eluter for a simplified SPE system that reduces the different types of equipment required.

It is a further object of the invention to provide such eluter that reduces the handling of sample materials.

Another object of the invention is to provide such eluter that is simple and economical.

Other objects of the present invention, as well as particular features, elements, and advantages thereof, will elucidated in, or be apparent from, the following description and the accompanying drawing figures.

SUMMARY OF THE INVENTION

The present invention achieves the above objects, among others by providing, in a preferred embodiment, an eluter instrument for an SPE system, comprising a housing, an upper seal mounted in said housing for up and down motion with respect thereto, a lower seal mounted in said housing for up and down motion with respect thereto, and said upper seal and said lower seal being moveable between a first position in which said upper seal and said lower seal are spaced apart and not in proximity and a second position in which said upper seal and said lower seal are in proximity and spaced apart sufficiently only to clamp therebetween a first area of a plurality of areas of an SPE medium, said first area containing therein one or more compounds of interest, such as to permit elution of said one or more compounds of interest to another instrument.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Reference should now be made to the drawing, on which similar or Identical elements are given consistent identifying numerals throughout the various figures thereof, and on which parenthetical references to figure numbers direct the reader to the view(s) on which the element(s) being described is (are) best seen, although the element(s) may be seen also on other views This invention contributes toward streamlining the conventional SPE process. It minimizes the sample handling, allowing a higher number of samples to be efficiently processed. Instead of placing the Empore® material in the bottom of the wells in a 96 well plate, it is supplied in a sheet form. Additional manufacturing steps are required to provide 96 areas of Empore® material to isolate one from the other. This is done by forming a heat-sealed dam around each of the 96 areas, thereby preventing cross flow between wells.

Figure 1:
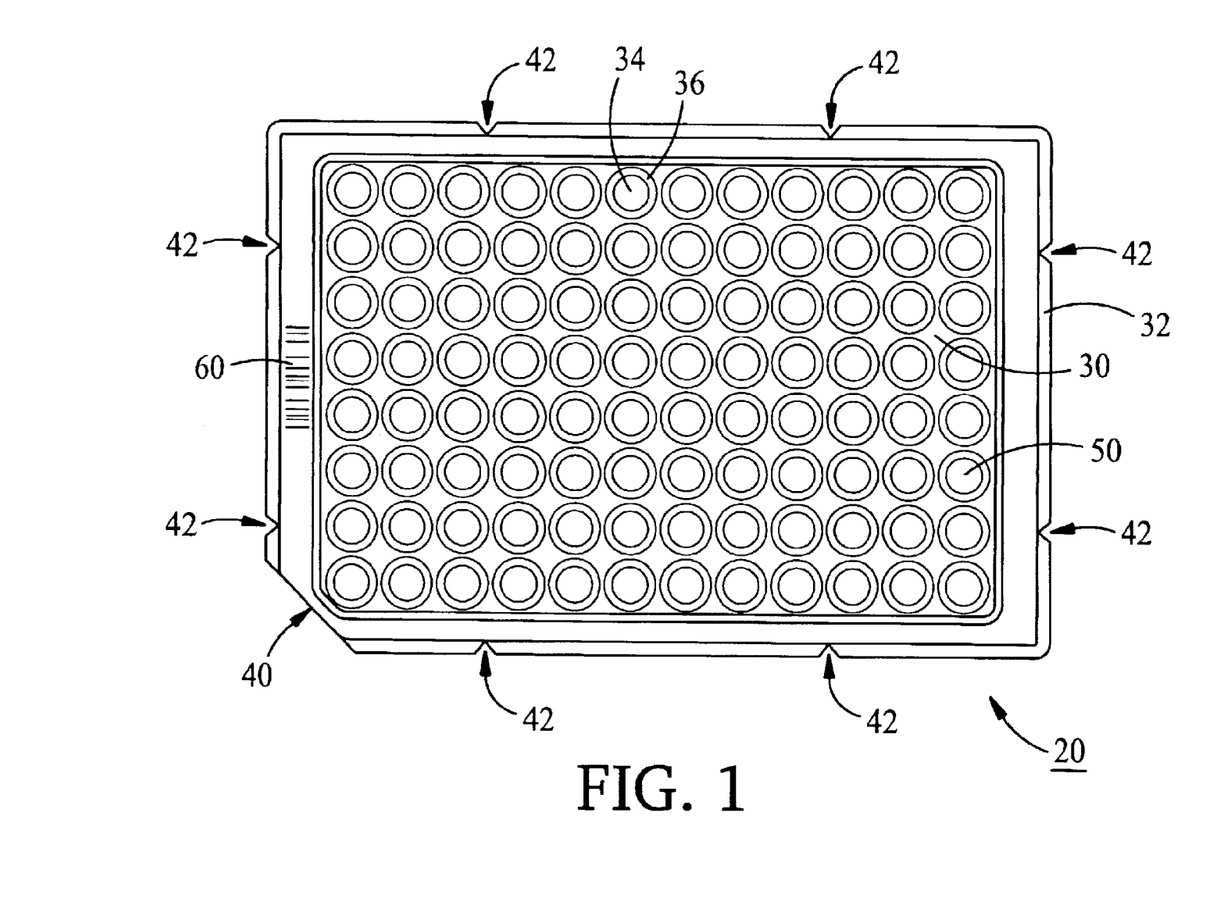
FIG. 1 is a top plan view of a solid phase extraction (SPE) plate.

This sheet of Empore® material is then placed in a modified conventional instrument, as further described below Using vacuum, the 96 original samples are passed from the sample plate directly through the Empore® material. The novel use of the conventional instrument has replaced the use of the pipettor for this transfer function. The modified conventional instrument is not only faster, but it is a less complex instrument than a multi-well pipettor and thus has a lower cost. The result is improved efficiency and a lower capital equipment cost The next step in the process is to elute the sample of interest from the Empore® material into the analysis instrument This invention has created an eluter instrument to accomplish this function. The eluter instrument simply places the required Empore® element directly in the injection pathway to the analyzer (HPLC or MS.). This eliminates the prior art method of eluting the sample into a capture plate and then moving the capture plate to the point of injection FIG. 1 illustrates a solid phase extraction (SPE) plate, generally indicated by the reference numeral 20. Plate 20 comprises a sheet of SPE material 30 mounted in an injection molded rectangular frame 32 SPE material 30 may be the Empore® material furnished by 3M company, as described above. SPE material 30 is about 0.030-inch thick and has a plurality of circular areas, as at 34, defined by a similar plurality of circular dams, as at 36, formed by the heat-sealing of the SPE material. Areas 34 are arranged in the 96-well format of an 8×12 matrix on 9 mm centers, with each of the well locations being defined and separated from the adjacent wells by heat-sealed dams 36, although other isolated well arrangements may also be employed.

Frame 32 includes an angled corner 40 for proper orientation in a sample transfer instrument, described below, and includes a plurality of triangular indents 42 defined around the perimeter thereof for precise positioning on a shuttle assembly, also described below Also provided on frame 32 is a bar code 60 that contains information as to the processing protocol for plate 20 Plate 20, as shown, meets the standard microplate footprint dimensions, established by the Society for BioMolecular Screening (SBS), and has a length of 5.030 inches and a width of 3.365 inches.

Figure 2:
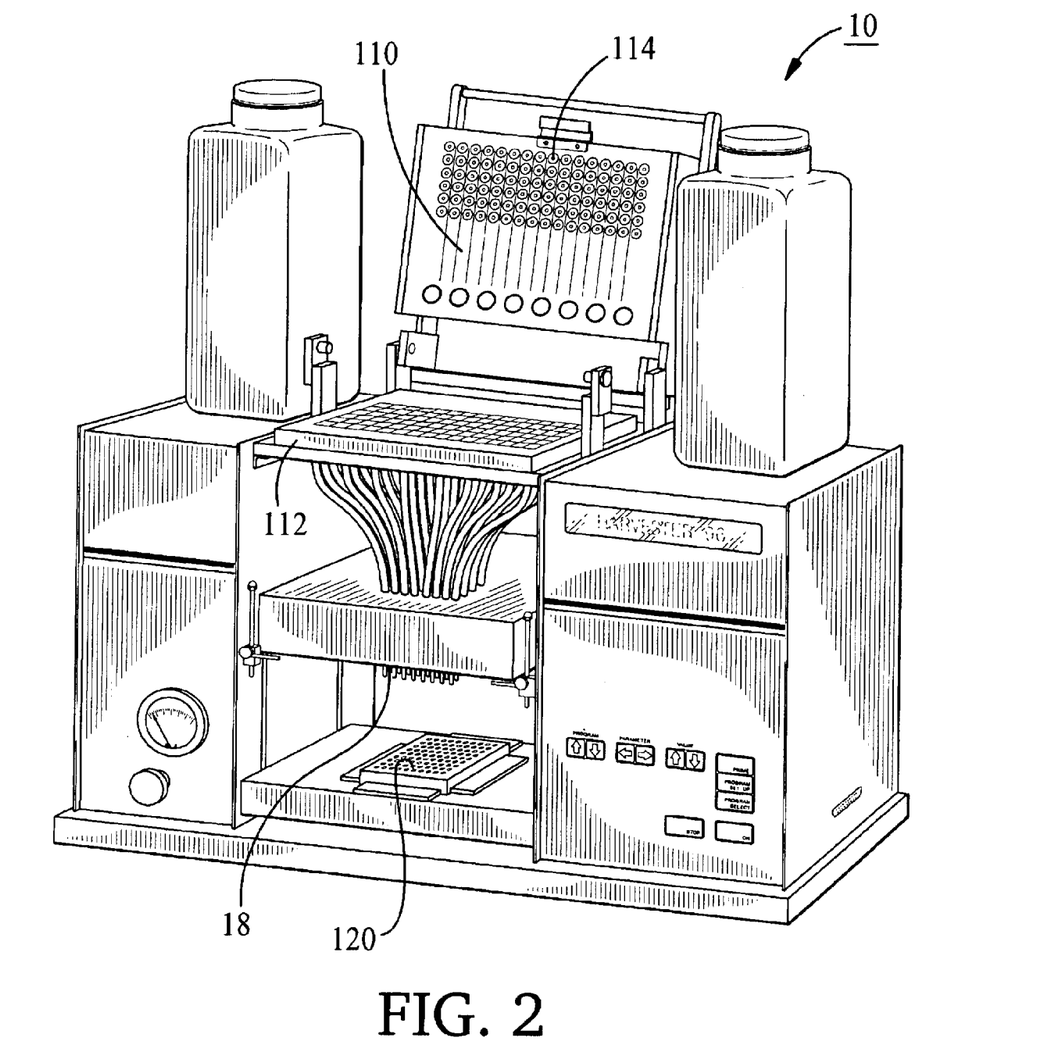
FIG. 2 is an isometric view of a sample transfer instrument.

FIG. 2 illustrates a sample transfer instrument, generally indicated by the reference numeral 100. The construction and operation of instrument 100 are similar to that of the instrument described in U.S. Pat. No. 5,648,266, issued Jul. 15, 1997, to Thomas W. Astle, and titled CELL HARVESTER SYSTEM, the disclosure of which is incorporated by reference hereinto The instrument described in the foregoing patent is modified for its use in the present invention by machining upper head assembly 110 and lower head assembly 112 to mate with SPE plate 20 (FIG. 1). Mating "O" rings 114 align with and mate to the 96-well configuration of SPE plate 20.

The operation of sample transfer instrument 100 is as described in the foregoing patent. A set of incoming samples in the 96-well format of a microplate is placed on input platform 120 which is raised to come into contact with aspirating head assembly 120. The incoming samples to be tested, contained in the sample plate, are drawn directly through the solid phase extraction media in SPE plate 20 (not shown) disposed between upper head assembly 110 and lower head assembly 114, with one or more compounds of interest being retained in the solid phase extraction media. The use of a pipettor as is currently used to accomplish this task, is eliminated This adds further to the utility of the process by eliminating equipment and a process step. SPE plate 20 has a defined orientation in transfer instrument 100

In those applications in which a solvent or other prewet of SPE media 30 (FIG. 1) is required, a reservoir of the solvent may be provided and aspirated through the SPE media with vacuum. The solvent reservoir is then replaced with the sample microplate and the samples aspirated to SPE media 30 If desired, another wash solution may follow the sample. SPE plate 20 with its 96 contained samples is then moved to an elution instrument, described below Other details of the construction and operation of sample transfer instrument 100 may be had by reference to the foregoing patent.

Figure 3:
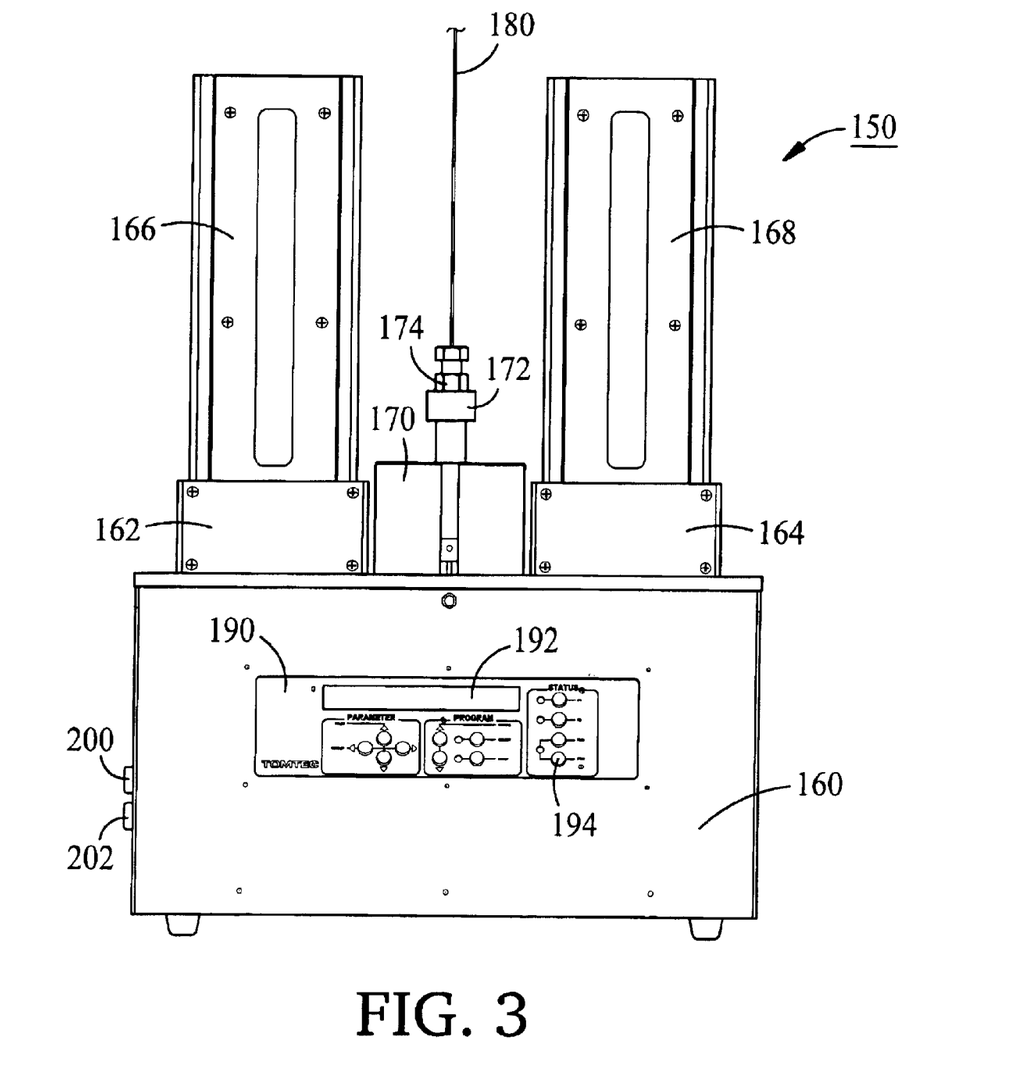
FIG. 3 is a front view of an elution instrument according to the present invention.

FIG. 3 illustrates an elution instrument, generally indicated by the reference numeral 150 for use following the above step. Elution instrument 150 includes a cabinet base 160 on which are mounted first and second stacker assemblies 162 and 164, the latter having removably mounted thereon, respectively, first and second cassettes 166 and 168 one or both containing a plurality of stacked SPE plates 20 from the above step. Also shown extending from the top of cabinet base 160 is an upper air cylinder 170, the function of which is described in detail below, and at the top of the upper air cylinder is an adjustable stop 172 and a cooperating adjustable stop nut 174 which limit the downward movement of a piston disposed in the upper air cylinder. A 0.010-inch diameter tube 180 extends from the upper end of upper air cylinder 170 and is connected (not shown) to an HPLC or MS instrument.

Mounted on the face of cabinet base 160 is an operator's panel 190 that includes a single line display 192 and a plurality of push button controls, as at 194. Extending from the side of cabinet base 160 are two high-pressure chromatography fittings 200 and 202 for connection (not shown) to a bypass loop.

Figure 4:
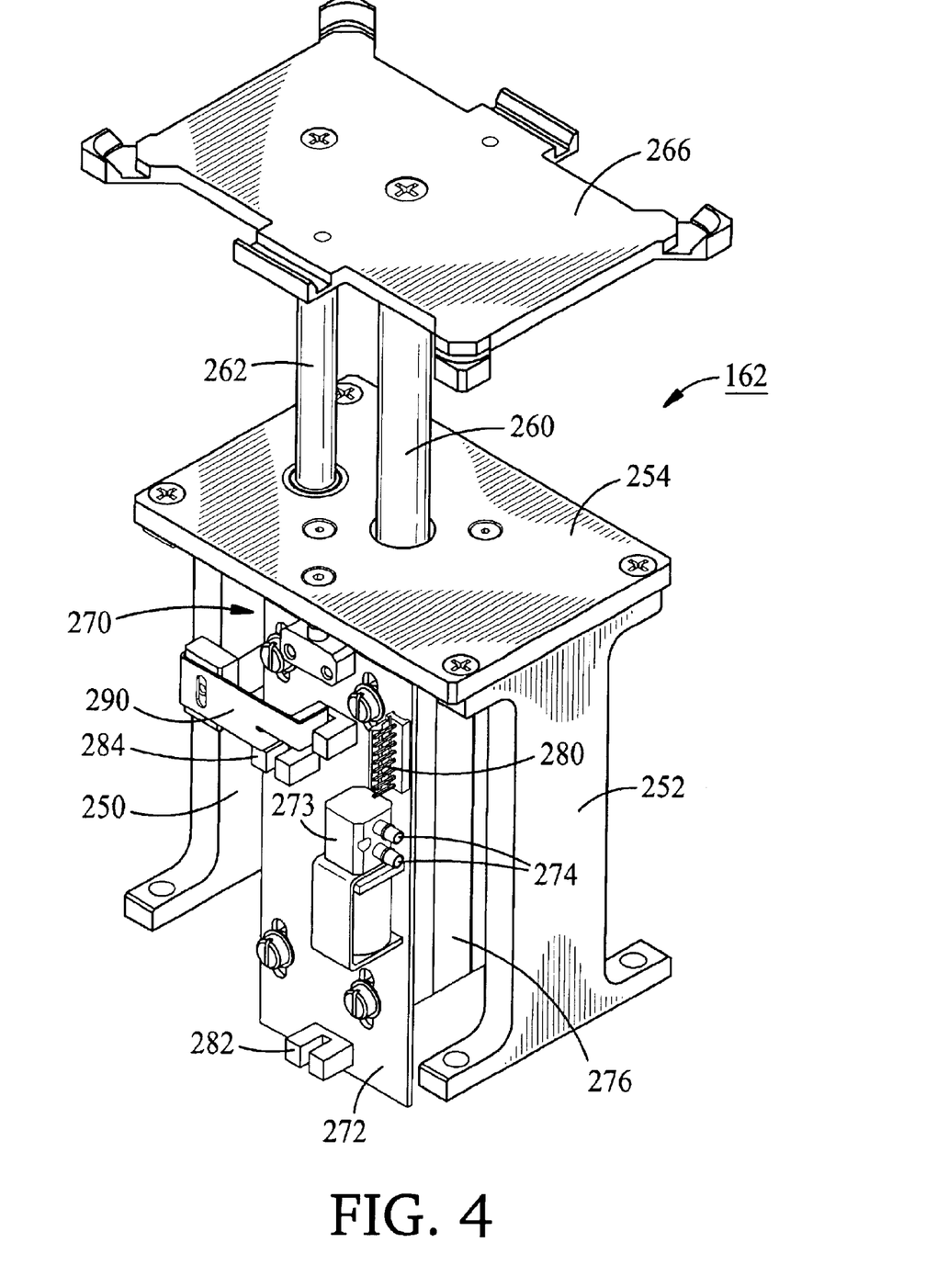
FIG. 4 is an isometric view of a stacker device used in the elution instrument of FIG. 3.

FIG. 4 illustrates the major elements of stacker assembly 162. Stacker assembly 162 includes first and second side vertical support/mounting brackets 250 and 252 on which is mounted a horizontal intermediate plate 254. Extending vertically from horizontal upper plate 254 are an air cylinder shaft 260 and an anti-rotation guide rod 262, both with their distal ends attached to and terminating at a horizontal nest plate 266.

Disposed generally within a volume 270 defined by first and second side support/mounting brackets 250 and 252 and intermediate plate 254 is a printed circuit board 272 on which is mounted a solenoid air valve 273 having connections 274 to supply control air to a square air cylinder 276 in which air cylinder shaft 260 is disposed for up and down movement (tubing between the connections and the air cylinder not shown) Also mounted on printed circuit board 272 are a electronic connector 280 and first and second position light switches 282 and 284. The latter two elements cooperate with a flag 290 operatively connected to air cylinder shaft 260 to indicate upper and lower positions of the shaft.

Figure 5:
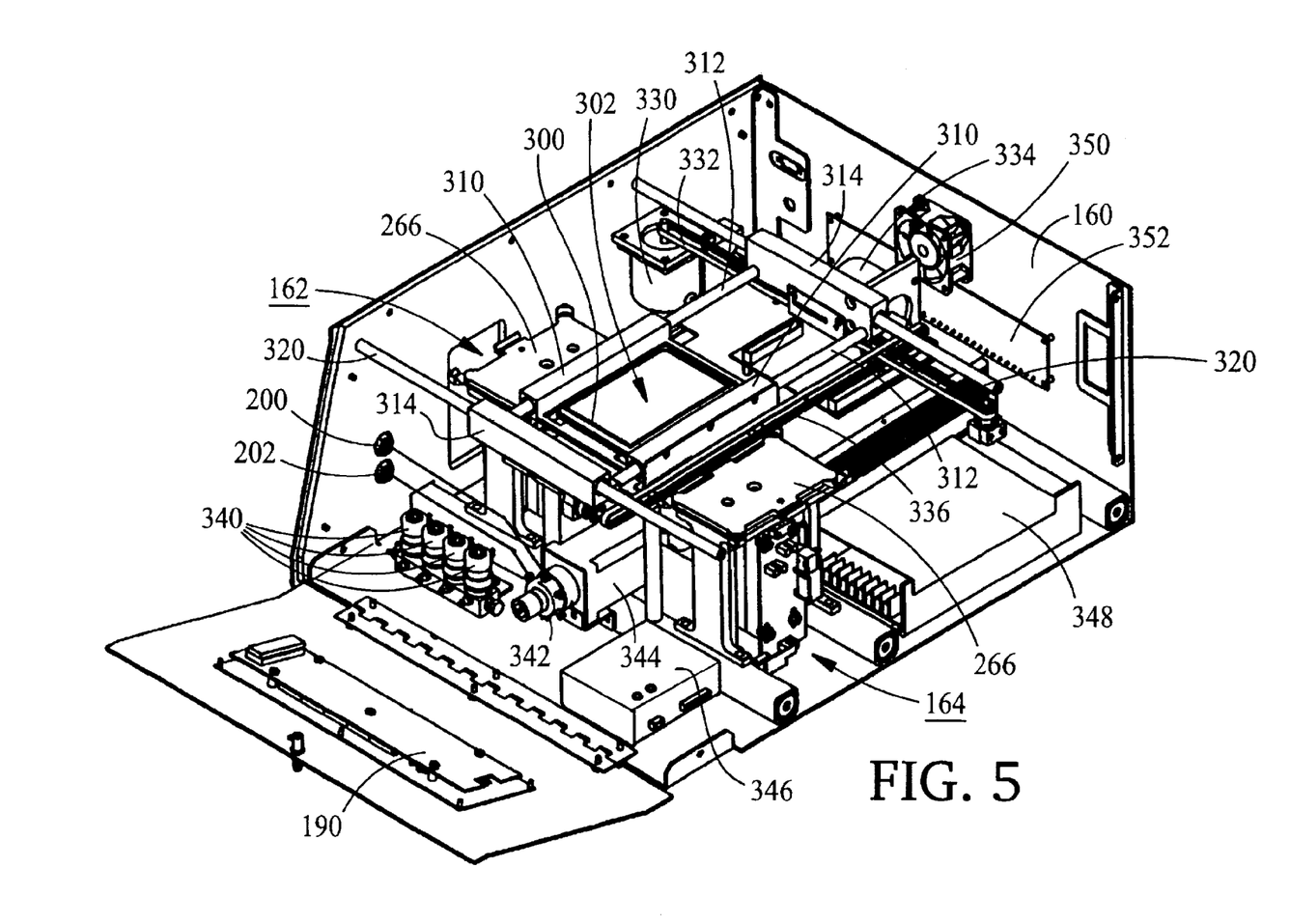
FIG. 5 is a cut-away isometric view of the elution instrument, with the top and right side removed and with the front operator's panel folded down.

FIG. 5 illustrates the major internal elements of cabinet base 160 (FIG. 3) which include stacker assemblies 162 and 164, the major elements of which have been described with reference to FIG. 4. Disposed generally centrally of cabinet base 160, as shown on FIG. 5, is a horizontal shuttle 300 having defined therethrough a shuttle opening 302. Shuttle 300 is fixedly disposed between two horizontal Y-motion bearing blocks 310 that are journaled on two horizontal Y-motion guide rods 312 fixedly disposed between two horizontal X-motion bearing blocks 314. X-motion bearing blocks 314 are journaled on two X-motion guide rods 320 disposed between opposite sides of cabinet base 160. A software-controlled X-motion stepper motor 330, an X-motion drive belt 332, a software-controlled Y-motion stepper motor 334, and a Y-motion drive belt 336 provide the necessary X-Y motion for shuttle 300. Cabinet base 160 also houses four cassette escapement control valves 340, a rotary valve 342 connected to external connections 200 and 202, a rotary valve drive motor 344, rotary valve drive motor power supply and controller 346, an electronics power supply 348, a cooling fan 350, and a connection panel 352

In operation, one of stacker assemblies 162 and 164, say stacker assembly 162, serves as an infeed to the system, while the other stacker, say stacker assembly 164, may serves as an outfeed to the system. Shuttle 300 is moved over nest plate 266 on stacker assembly 162. Nest plate 266 is moved through shuttle opening 302 and an air cylinder (not shown on FIG. 5) opens an escapement releasing a SPE plate 20 (FIG. 1) from cassette 166 (FIG. 3) to the nest plate. The escapement closes, to retain the next plate in cassette 166. As nest plate 266 lowers, it passes through shuttle opening 302, depositing SPE plate 20 on shuttle 300. Triangular points 42 (FIG. 1) formed on SPE plate 20 precisely position the SPE plate on shuttle 300. Shuttle 300 is then moved to the position shown on FIG. 5 for elution, as is described below. After all areas 34 have been sampled, finished SPE plate 20 is positioned by shuttle 300 under outfeed stacker, 164. The process then repeats for the next SPE plate 20

Figure 6:
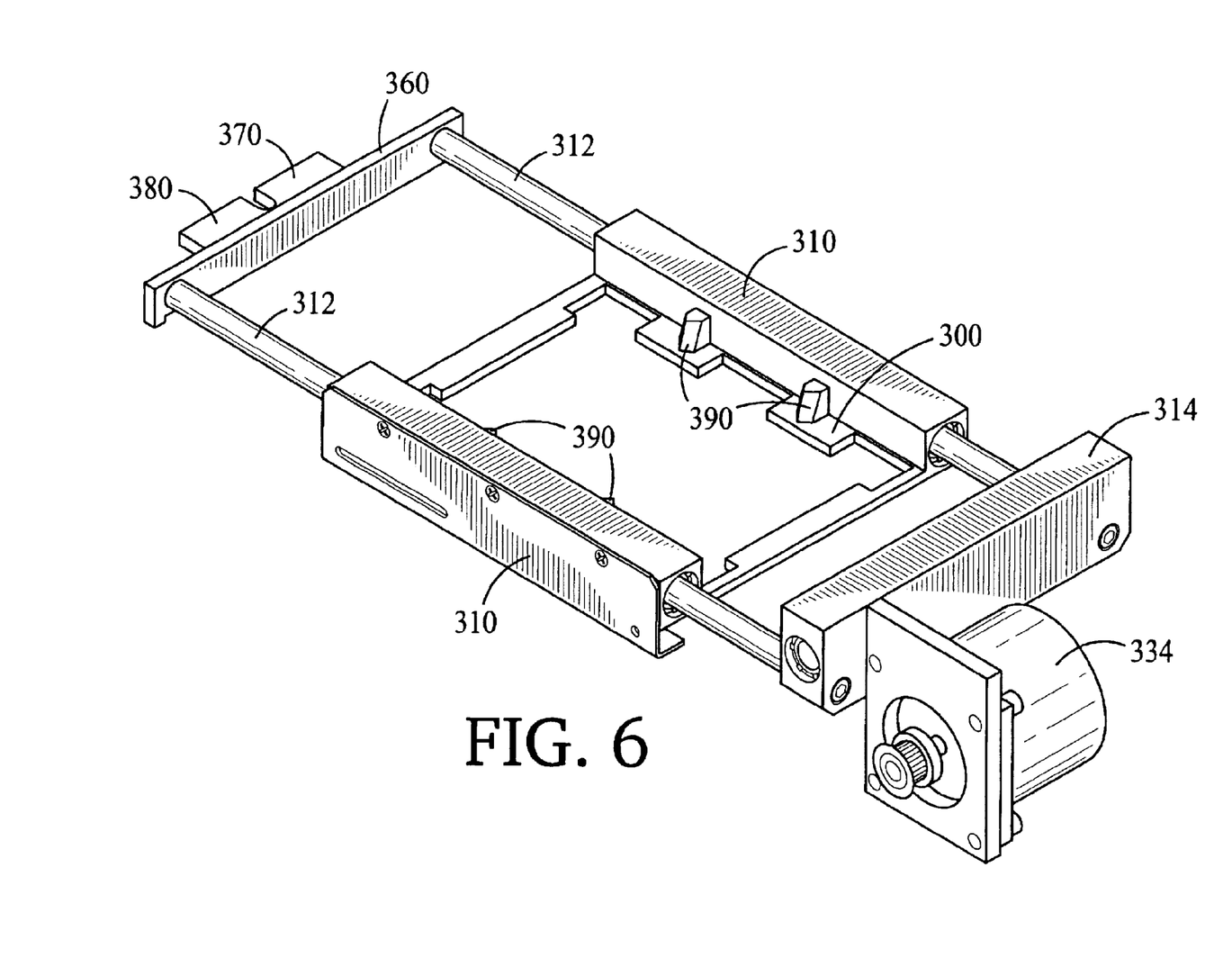
FIG. 6 is a fragmentary isometric view of an X-Y shuttle assembly, less the X-motion components and the Y-motion drive belt used in the elution instrument.

FIG. 6 illustrates in more detail the construction of shuttle 300. Here it can be seen that one set of ends of Y-motion guide rods 312 terminates at a horizontal member 360. A tab 370 extending outwardly from horizontal member 360 is pinned at a single point to front X-motion bearing block 314 (FIG. 5, not shown on FIG. 6). This single point of attachment accommodates misalignment of X-motion bearing blocks 314. A second tab 380 extends outwardly from front bearing block 314 and activates an optical switch to indicate when shuttle 300 is fully forward. Four locating triangles 390 engage notches 42 (FIG. 1) on SPE plate 20 to align the SPE plate on shuttle 300.

Figure 7:
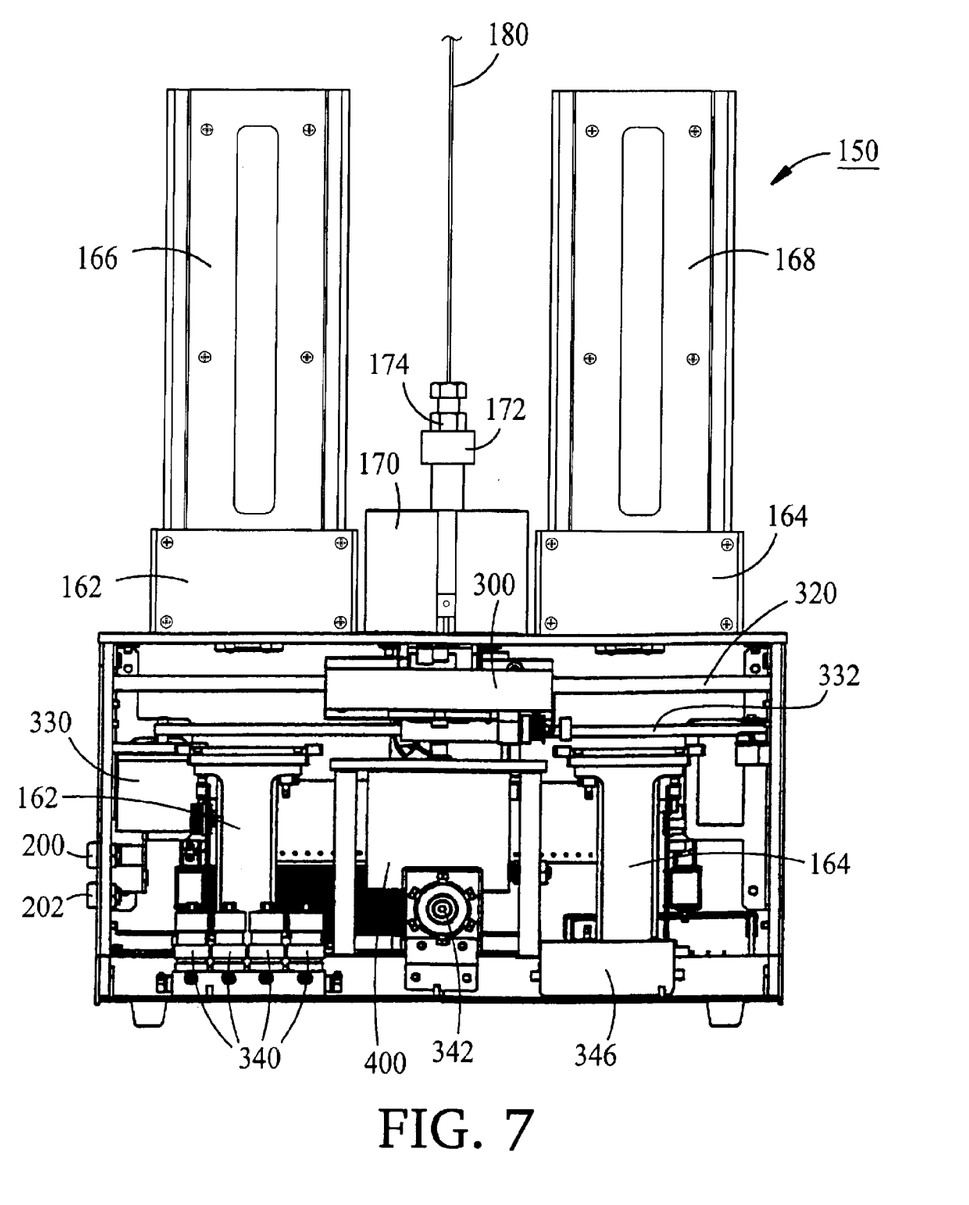
FIG. 7 is a front elevational view of the elution instrument, with the front panel thereof removed.

FIG. 7 illustrates further the arrangement of some of the elements shown on FIGS. 3–6 and further illustrates the location of a lower air cylinder 140.

Figure 8:
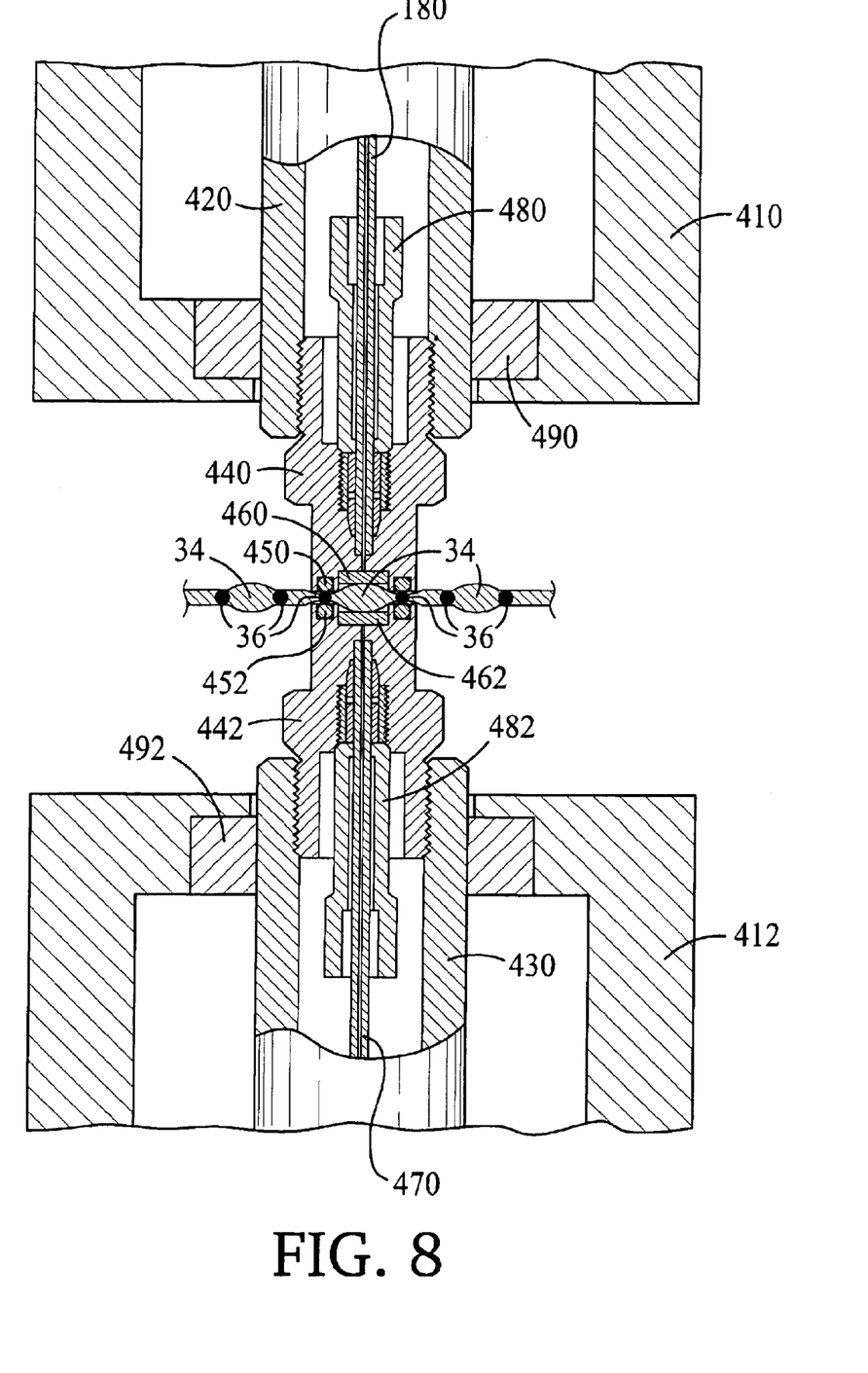
FIG. 8 is a front elevational view, in cross-section, of the air upper and lower cylinders that provide the closing action of the "O" rings clamping the SPE plate for elution, with an SPE material clamped in position.

FIG. 8 illustrates a fixed body 410 of upper air cylinder 170 (FIG. 7) disposed vertically over a fixed body 412 of lower air cylinder 400 (FIG. 7). Upper air cylinder body 410 has disposed therein for up and down motion with respect thereto an upper piston 420, while lower air cylinder body 412 has disposed therein for up and down motion with respect thereto a lower piston 430, the upper and lower pistons being vertically aligned. Extending downwardly coaxially from upper piston 420 is an upper connector 440 and extending upwardly coaxially from lower piston 430 is a lower connector 442. Upper and lower O-rings 450 and 452 disposed, respectively, around the distal ends of upper and lower connectors 440 and 442 are shown clamping therebetween a heat-sealed dam 36 (FIG. 1) and, therefore, an area 34. Indexing of sheet 30 will permit other areas 34 to be clamped between upper and lower O-rings 450 and 452. It will be understood that area 34 has been clamped between upper and lower O-rings 450 and 452 by means of upper piston 440 moving downwardly and lower piston 442 moving upwardly. O-rings 450 and 452 prevent flow between areas 34, commonly referred to as "cross talk".

Upper and lower horizontal circular stainless steel frits 460 and 462 are provided, respectively, in the distal ends of upper and lower connectors 440 and 442 to spread out liquid flowing upwards from tube 470 connected to rotary valve 342 (FIG. 5), across area 34, and into tube 180 Tubesl 80 and 47o are disposed, respectively, in upper and lower chromatography connectors 480 and 482 axially centrally disposed in upper and lower connectors 440 and 442 Annular upper and lower piston guides and bearing and seals 490 and 492 are disposed, respectively, between upper and lower pistons 420 and 422 and upper and lower air cylinder bodies 410 and 412.

A software program activates upper air cylinder 170 (FIG. 7) first. It has a larger bore than lower air cylinder 400, thus upper air cylinder 170 can generate more force with an equivalent air pressure Piston 420 moves downwardly to a depth set by adjustable stop 172. This brings upper O-ring 450 into contact with sheet 30. Lower air cylinder 400 is then energized, forcing lower O-ring 452 to mate with upper O-ring 450, thereby sealing a specific area 34 in sheet 30 to be eluted. Motor operated rotary valve 342 (FIG. 5), as commonly used in high performance liquid chromatography, switches the solvent flow path to the analysis instrument (not shown), so as to put the desired clamped area 34 in the flow path The solvent elutes the sample from area 34, transporting it to the analysis instrument, usually HPLC or MS. After the operator-set elution time expires, the next sequence is enabled.

If eluter 150 is set up to clamp a row of areas 34 at a time, then another selector valve, common to HPLC use, switches the flow path to the next clamped area. The elution step repeats for this area 34 and the next, until all areas in that clamped row have been eluted.

After all clamped areas 34 have been eluted (single area or multiple areas), the solvent flow path to the analysis instrument is switched to bypass eluter 150. Upper and lower air cylinders 170 and 400 retract to clear plate 20 on shuttle 300. Stepper motors 330 and/or 334 move shuttle 300 to the next desired position, and the above stated sequence repeats for the next clamped area or areas 34

Following elution of all areas 34 in the program for that particular plate 20, shuttle 300 moves the plate to align with whichever of stacker assemblies 162 and 164 is the outfeed. An operating air cylinder associated with that stacker lifts plate 20 from shuttle 300 by passing through shuttle opening 302. Plate 20 is carried up into cassette 166 or 168. An escapement in that stacker opens to allow incoming plate 20 to pass through and then closes to retain the plate. The entire sequence is then repeated for the next plate 20

Figure 9:
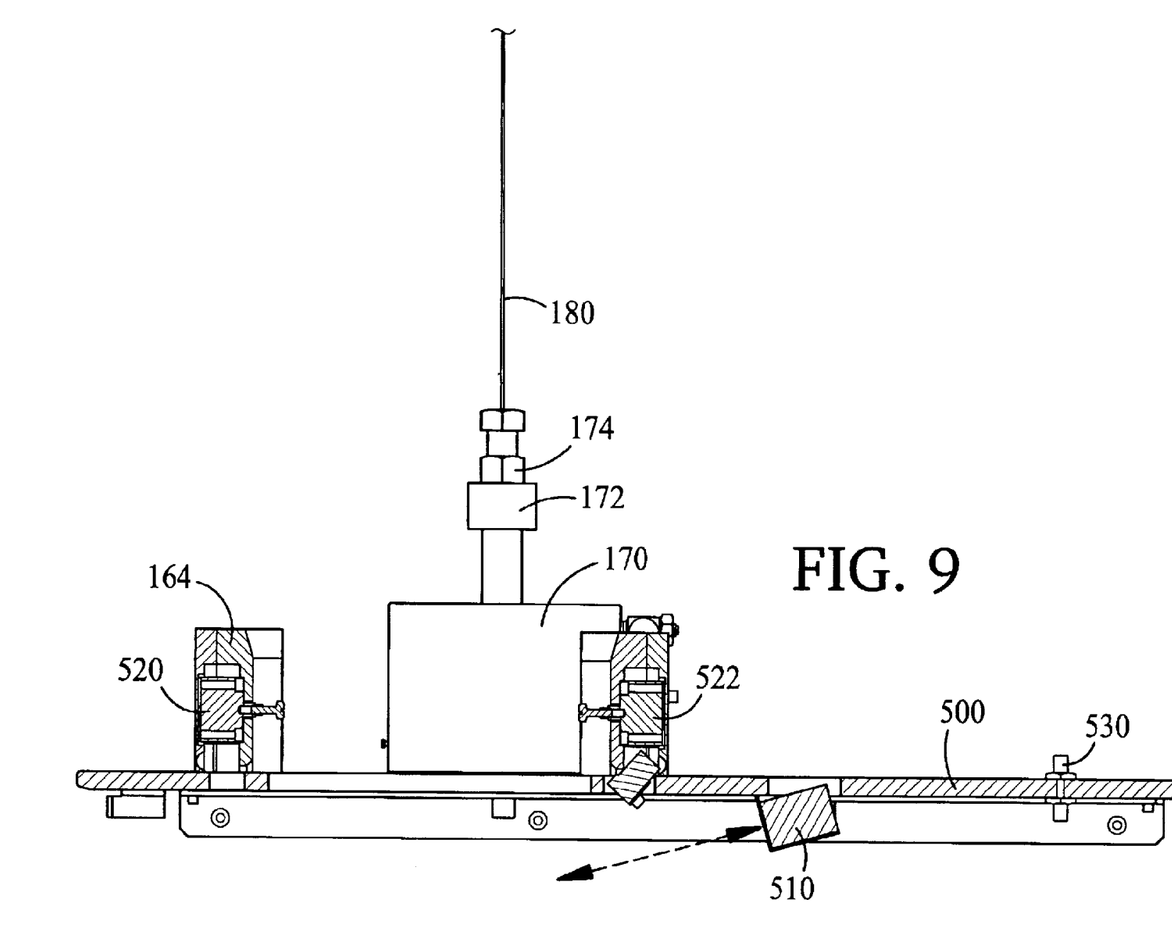
FIG. 9 is a fragmentary, side elevational view, in cross-section, of a stacker assembly, less the cassette for handling SPE plates

FIG. 9 illustrates upper air cylinder 170 mounted on upper deck 500 of cabinet base 160 (FIG. 3) and also a bar code reader 510 that scans bar code 60 (FIG. 20) on incoming SPE plates 20 while on shuttle 300 (FIG. 5, not shown on FIG. 9). Also shown on FIG. 9 are stacker 164, with first and second escapement assembly air cylinders 520 and 522, respectively, and a fitting 530 for air to upper air cylinder 170.

Figure 10:
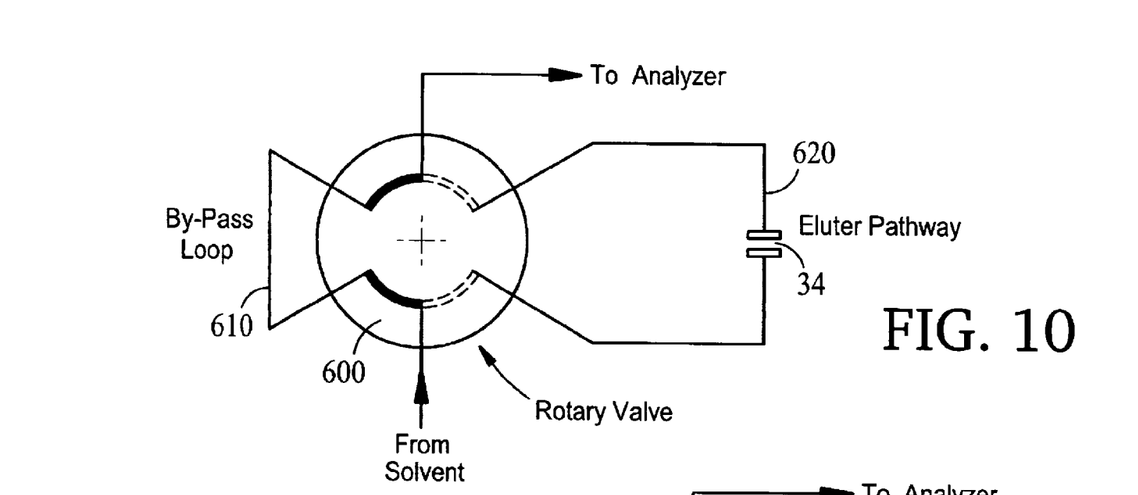
FIG. 10 is a schematic flow diagram showing the elution pathway with a single well elution design.

FIG. 10 illustrates the flow pathway for a single elution. When rotary valve 600 is set so that the solvent pathway is along the solid lines in the valve, the solvent will flow through bypass loop 610 When, however, rotary valve is rotated 180 degrees, solvent flow will be through cluter pathway 620 and an area 34 (FIG. 8).

Figure 11:
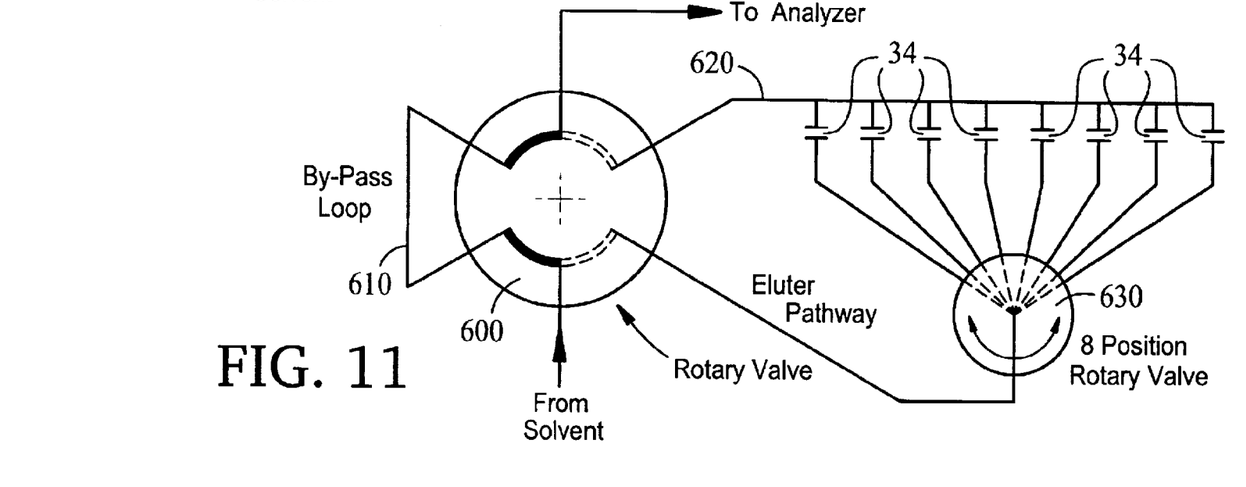
FIG. 11 is a schematic flow diagram showing the elution pathway, with a design that can elute multiple wells in a row by moving the shuttle holding the SPE plate.
Figure 12:
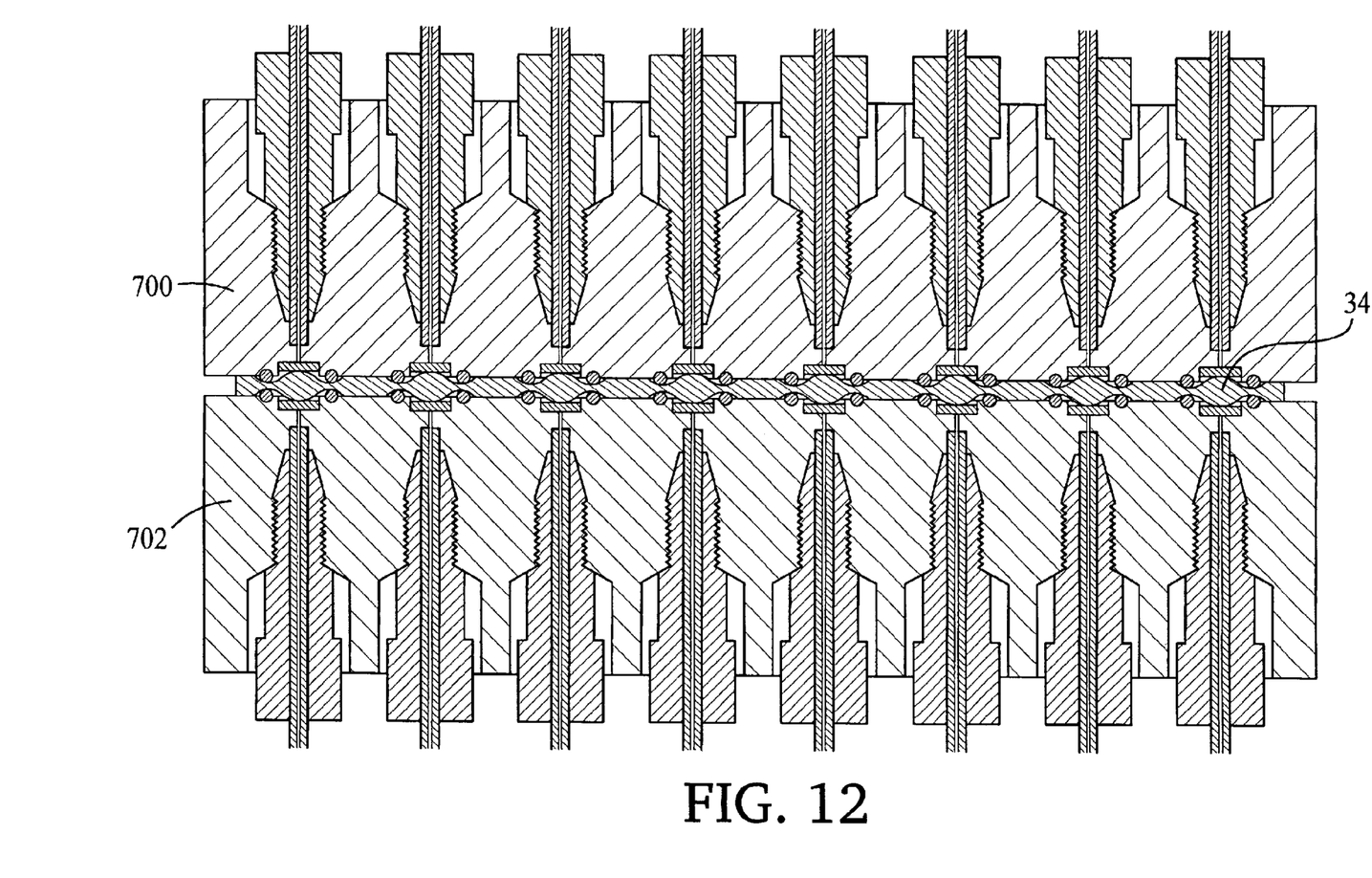
FIG. 12 is a side elevational view, in cross-section, of an eight-place elution head.

FIG. 11 illustrates the same rotary valve 600, bypass loop 610 and eluter pathway 620. In this case, however, a second rotary valve 630 is disposed in eluter pathway 620 to select one of eight areas 34 through which solvent will flow. In this case, it is assumed that all eight areas 34 shown are clamped in a suitable elution instrument and that the eight areas represent one eight-area row on an SPE plate 20 (FIG. 1). If a 12-area row on SPE plate 20 is clamped, any one of twelve areas 34 could accessed and second rotary valve 630 would have twelve positions. The advantage of either arrangement is time-savings Second rotary valve 630 can switch sample locations faster than the eluter head can open to permit shuttle 300 (FIG. 5) to reposition and then close to sample the next well location FIG. 12 illustrates an eight-place elution head Here eight areas, as at 34, are clamped Clamping is accomplished by means of an upper clamping member 700 being lowered by upper air cylinder 170 (FIG. 7) and a lower clamping member 702 being raised by lower air cylinder 400 (FIG. 7). The various elements of upper and lower clamping members 700 and 702 are similar to those described with reference to FIG. 8.

The control system for eluter 150 (FIG. 7) is an embedded microprocessor and its associated circuitry, combined with a specific software program. This allows an operator to control the system as deemed necessary Individual sequences can be performed for trouble shooting or set up. Preset sequences can be executed for the convenience of the operator. The software provides various elution sequences that may be programmed and operated by the user. Sequences of areas by row or individually can be set Single line display 192 (FIG. 3) is used for communication between the operator and the controlling software. Preset programs can be created and run at the press of a START button. A stack of SPE plates 20 can be loaded and processed automatically without operator attention.

Data tracking is provided by means of bar code reader 510 (FIG. 9) that reads identifying bar code 60 (FIG. 1) on each frame 32. Bar code identifier 60 provides an audit trail of a specific plate 20 and this data may be printed out through an RS232 port on the instrument to a receiving device Complex programs may be created to sample only certain defined wells on specific frames 32. The ability of stackers 162 and 164 (FIG. 7) to serve as either infeed or outfeed permits plates 20 to move back and forth between cassettes 166 and 168, while searching for a specific bar code 60. Eluter 150 then performs the desired operation on that specific SPE plate 20.

To summarize the differences between this system and the prior art, this system is used in a two-step direct pathway. The sample is collected on the SPE medium and eluted directly from that medium into the analyzer. This achieves both throughput and efficiency in the process. The multi-well pipettor used for sample transfer has been replaced with a faster, lower-cost instrument. The auto sampler, normally used to feed samples to the injector, has been replaced with the eluter, described by this patent application. The Empore® media in a plate type format combined with the eluter provides a very high throughput efficient system. The eluter stackers can completely automate an extensive run of samples A side benefit of the efficiency of this new system is the conservation of disposables. The Empore® media plate consumes far less plastic than is presently used in SPE plates. The pipettor tips and the capture plates of conventional methods are also eliminated.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. An eluter instrument for an SPE system, comprising:
   (a) a housing for an eluter instrument;
   (b) an upper seal mounted in said housing with apparatus for moving said upper seal in up and down motion with respect to said housing;
   (c) a lower seal mounted in said housing with apparatus for moving said lower seal in up and down motion with respect to said housing;
   (d) an SPE medium disposed between said upper seal and said lower seal;

(e) said upper seal and said lower seal being moveable between a first position in which said upper seal and said lower seal are spaced apart and not in proximity and a second position in which said upper seal and said lower seal are in proximity and spaced apart sufficiently only to clamp therebetween a first area of a plurality of areas of an SPE medium, said first area containing therein one or more compounds of interest;

(f) apparatus to elute said one or more compounds of interest sequentially from said plurality of areas to another, single instrument; and (g) apparatus to introduce said SPE medium to and remove said SPE medium from a treatment area of said eluter instrument.

2. An eluter instrument for an SPE system, as defined in claim 1, wherein: said upper seal and said lower seal are O-rings.

3. An eluter instrument for an SPE system, as defined in claim 1, wherein: said upper seal and said lower seal engage surfaces of a dam formed around said first area.

4. An eluter instrument for an SPE system, as defined in claim 3, wherein: said dam is formed by heat-sealing a portion of said SPE medium.

5. An eluter instrument for an SPE system, as defined in claim 1, further comprising: apparatus to automatically move said SPE medium and clamp a second area of said SPE medium between said upper seal and said lower seal.

6. An eluter instrument for an SPE system, as defined in claim 5, wherein: said apparatus includes first and second stackers for stacking a plurality of frames containing a plurality of SPE media such that said frames can be fed in and out of an elution station automatically without operator handling.

7. Au eluter instrument for an SPE system, as defined in claim 6, further comprising: means for reading identifying indicia on said frames, combined with software, to generate a data audit trail of each incoming said frame, with processing parameters for each frame contained in said identifying indicia.

8. An eluter instrument for an SPE system, as defined in claim 1, further comprising: a first fit disposed above said first seal and a second fit disposed below said second seal, said first fit and said second frit to distribute eluent solvent across said first area.

9. An eluter instrument for an SPE system, comprising:

(a) a housing for an eluter instrument;

(b) a plurality of upper seals mounted in said housing with apparatus for moving said upper seals in up and down motion with respect to said housing;

(c) a plurality of lower seals mounted in said housing with apparatus for moving said lower seals in up and down motion with respect thereto;

(d) said upper seals and said lower seals being moveable between a first position in which said upper seals and said lower seals are spaced apart and not in proximity and a second position in which said upper seals and said lower seals are in proximity and spaced apart sufficiently only to clamp therebetween a plurality of areas of an SPE medium, said plurality of areas containing therein one or more compounds of interest;

(e) apparatus to elute said one or more compounds of interest sequentially from said plurality of areas to another, single instrument;

(f) valving to selectively and sequentially select one of said plurality of areas from which to elute said one or more compounds of interest; and (g) apparatus to introduce said SPE medium to and remove said SPE medium from a treatment area of said eluter instrument.

10. An eluter instrument for an SPE system, as defined in claim 9, wherein: said valving is automatically controlled to select one of said plurality of areas from which to elute said one or more compounds of interest.

* * * * *